(12) United States Patent
Alberico et al.

(10) Patent No.: US 8,309,744 B2
(45) Date of Patent: Nov. 13, 2012

(54) PROSTAGLANDIN SYNTHESIS AND INTERMEDIATES FOR USE THEREIN

(75) Inventors: Dino Alberico, Mississauga (CA); Joshua Clayton, Oakville (CA); Boris Ivanovich Gorin, Oakville (CA); Jan Oudenes, Aurora (CA)

(73) Assignee: Alphora Research Inc., Mississauga (CA)

( * ) Notice: Subject to any disclaimer, the term of this patent is extended or adjusted under 35 U.S.C. 154(b) by 0 days.

(21) Appl. No.: 13/081,794

(22) Filed: Apr. 7, 2011

(65) Prior Publication Data

US 2011/0184192 A1  Jul. 28, 2011

Related U.S. Application Data

(62) Division of application No. 12/271,374, filed on Nov. 14, 2008, now Pat. No. 7,928,252.

(30) Foreign Application Priority Data

Aug. 29, 2008 (CA) ..................... 2639240

(51) Int. Cl.
C07D 307/00 (2006.01)
C07D 307/93 (2006.01)
C07D 311/00 (2006.01)
C07D 61/06 (2006.01)

(52) U.S. Cl. ......... 549/299; 549/465; 549/396; 562/503

(58) Field of Classification Search .......... 549/299, 549/465, 396; 562/503

See application file for complete search history.

(56) References Cited

U.S. PATENT DOCUMENTS 5,252,605 A   10/1993   Ueno

Primary Examiner — Nizal Chandrakumar
(74) Attorney, Agent, or Firm — McMillan LLP

(57) ABSTRACT

Fused cyclopentane—4-substituted 3,5-dioxalane lactone compounds useful as an intermediate in the synthesis of prostaglandin analogs are provided. The compounds have the formula A:

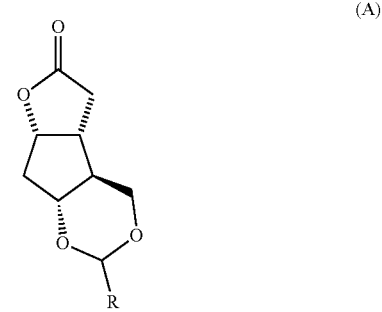

(A)

wherein R represents an aryl group such as p-methoxyphenyl. This compound can be reacted with a lower alkyl aluminum compound to open the dioxalane ring and reduce the lactone to lactol, without over-reducing to diol. The resulting compound can be functionalized to insert chemical side groups of target prostaglandins, adding the required α-side chain and then the required ω-side chain sequentially and independently of each other. The compounds and process are particularly suitable for preparing lubiprostone.

6 Claims, 1 Drawing Sheet

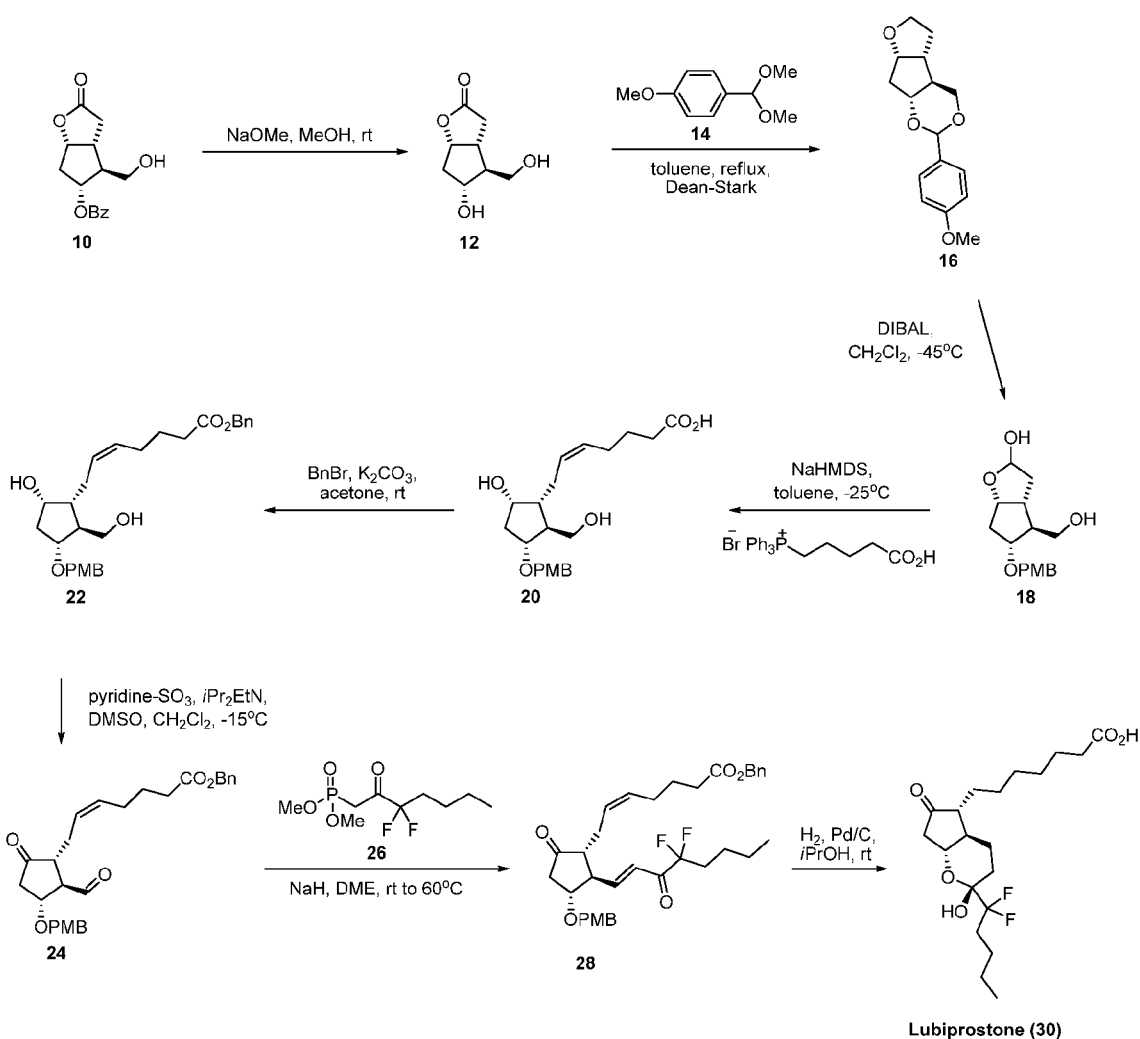

PROSTAGLANDIN SYNTHESIS AND INTERMEDIATES FOR USE THEREIN

FIELD OF THE INVENTION

This invention relates to prostaglandin analogs and their synthesis. More particularly, it relates to a novel, simplified synthesis of prostaglandin analogs, and novel chemical compounds useful as intermediates in such synthesis.

BACKGROUND OF THE INVENTION AND PRIOR ART

Prostaglandins (PGs) are organic carboxylic acids, namely cyclopentanes carrying two side chain substituents, typically linear C6-C8 side chains, bonded to adjacent positions on the cyclopentane nucleus. One of the side chains, the α-side chain, carries a terminal carboxylic acid group. Many are natural products found in mammalian organs and tissues (primary PGs), and exhibit a variety of physiological activities. Primary PGs generally have a prostanoic acid skeleton, which forms the basis of the nomenclature:

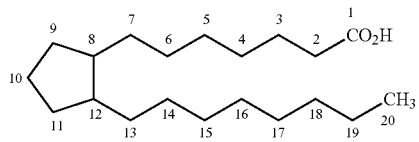

A significant number of synthetic PG analogs have been made and found to have useful pharmacological properties. These may have modified skeletons, and substituted and unsaturated side chains. PGs are characterized by a hydroxyl (or ketone) substituent on the cyclopentane nucleus, position 9.

Prostaglandin analogs are difficult to synthesize. Complications arise because of the requirements of the end products to have several functional groups and two side chains of significant size and complexity. Stereospecificity is commonly required, for substituent groups and for bonds in the core. Since the products are intended for pharmaceutical use, the range of industrially acceptable reagents, solvents, catalysts, etc. which can be used in their synthesis is limited to those having pharmaceutical industry acceptability.

A common starting material for PG analog synthesis is the commercially available Corey alcohol benzoate, of formula:

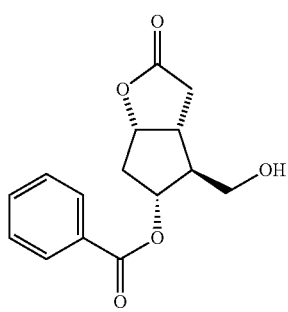

To convert this to a synthetic PG analog, many protection, functionalization, de-protection, etc. steps are required to form the desired side chains. U.S. Pat. No. 5,252,605 Ueno, issued Oct. 12, 1993, reports several PG syntheses starting from Corey alcohol which involve approximately fifteen steps. Inevitably, such a multi-step process is time consuming and expensive to conduct, and results in relatively low overall yield of final product.

An example of a synthetic prostaglandin analog of specific interest is lubiprostone, of formula:

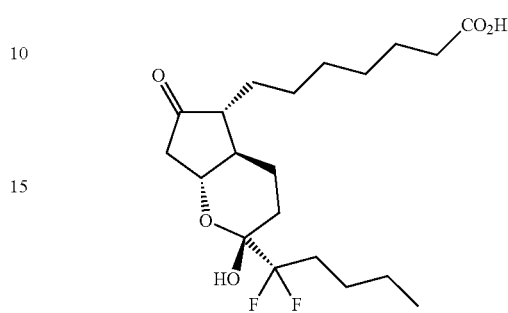

This compound is marketed as "Amitiza", for use in treatment of chronic idiopathic constipation, irritable bowel syndrome and post-operative ileus. Its synthesis presents significant technical challenge because of the chemical complexity of the fluorine containing substituent chain at the 12-position. Known methods for its synthesis suffer from the aforementioned disadvantages, namely a multi-step (typically 15-step) synthesis from Corey alcohol with consequent low yields of final product and time consuming nature of the process.

It is an object of the present invention to provide a novel synthetic method for preparing PG analogs, in fewer steps and in improved overall yield.

It is a further object to provide novel chemical compounds useful in the synthesis of PG analogs.

It is a specific object of the present invention to provide a novel synthesis of lubiprostone, starting from commercially available Corey alcohol.

SUMMARY OF THE INVENTION

One significant aspect of the present invention is a small class of novel chemical compounds comprising a cyclopentane nucleus fused at its 4,5 position with a 4-substituted 3,5-dioxalane ring, and fused at its 3a,6a-position with a lactone ring. The compounds have the formula:

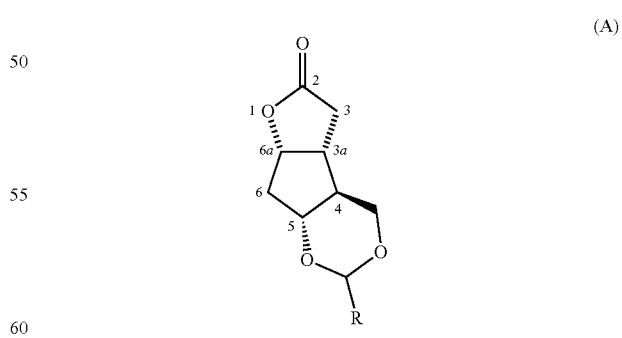

(A)

where R represents an aryl group, preferably a substituted phenyl group such as p-methoxyphenyl (PMP). Subsequent reaction of a compound of formula A with a lower alkyl-aluminum compound such as di-isobutyl aluminum hydride (DIBAL) under properly selected conditions causes ring opening of the dioxalane at a specific position, as well as reduction of the lactone to lactol without over-reducing the lactol ring structure to a diol. The product of the ring opening reaction has a hydroxymethyl group at position 1 on the cyclopentane nucleus, ready for chemical expansion to provide the ω-chain of the selected target PG analog, and a protected hydroxyl group at position 2. In subsequent steps, the lactol ring can be opened chemically, and expanded to form the β-chain of the target compound, with the residue of the lactol ring forming the basis for the eventual 9-hydroxy or 9-keto group of the target PG analog. The formation of this ring-opened product B may be represented as follows:

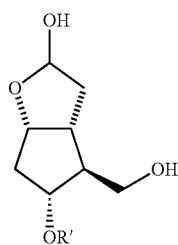

It is totally unexpected that this reaction should take place without over-reducing the lactone ring. One would have predicted formation of a complex mixture of different reduction products, with such a plurality of potentially reducible groups and sites being subject to such a powerful reducing agent as DIBAL. Instead, by selection of appropriate reaction conditions, a high degree of selectivity to from product B is achieved. These conditions include selection of a reaction solvent which is a good solvent for the cyclopentane compound, and which is a polar, non-co-ordinating solvent that permits, and does not interfere with, co-ordination of the aluminum complex with the available oxygen of the ring structure, to the substantial exclusion of co-ordination of the aluminum to the solvent itself; and temperatures appropriate to maintain the stability of the organo-aluminum compound. Suitable such solvents include methylene chloride, dichloroethane, chlorobenzene, chloroform, toluene and mixtures thereof, and similar polar hydrocarbons, with methylene chloride being most preferred. Preferably low temperatures, below 0° C. and most preferably in the −40-−50° C. range.

Thus according to a first aspect of the present invention, there is provided in one embodiment a fused cyclopentane—4-substituted 3,5-dioxalane lactone compound useful as an intermediate in the synthesis of prostaglandin analogs, the compound having the formula A:

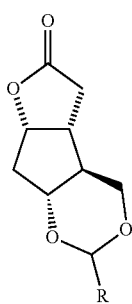

wherein R represents a lower alkoxy substituted phenyl group.

According to a second aspect, there is provided a process of preparing a substituted cyclopentane lactone compound of formula B, which comprises subjecting a compound of formula A as defined above to selective ring opening reduction with a lower alkyl-aluminum reducing agent in solution in a polar, non-coordinating solvent at a temperature at which the reducing agent is stable.

BRIEF REFERENCE TO THE DRAWING

The single FIG. 1 of accompanying drawings illustrates the overall reaction scheme embodying the present invention, in the preparation of lubiprostone, a preferred embodiment thereof.

DESCRIPTION OF THE PREFERRED EMBODIMENTS

Referring to the accompanying drawing FIG. 1, the preferred synthesis according to the invention starts with Corey alcohol benzoate 10, which is commercially available. Reaction of this with sodium methoxide in methanol (room temperature, 1.5 hours) produces Corey lactone diol 12 in high yield (e.g. 97%) ready for further reaction.

A cyclopentane-lactone-dioxalane fused tricyclic compound 16, member of the class of compounds A of the present invention, is prepared by reacting Corey lactone diol 12 with anisaldehyde dimethyl acetal, compound 14, in the presence of trace amounts of acid. This reaction suitably takes place under reflux, over a period of, for example 3 hours. A dioxalane ring substituted at ring position 2 with p-methoxyphenyl (PMP) forms in high (85-90%) yield. In the next step, according to this preferred embodiment of the process, compound 16 is reacted with DIBAL, in solution in methylene chloride and toluene, and at a low temperature (e.g. −45° C.) at which DIBAL is stable. Ring opening of the dioxalane at a specific position occurs, without over-reduction the lactone structure to diol, thereby producing compound 18, a representative of class B referred to above, in a yield in excess of 80%. Compound 18 has a hydroxymethyl group at position 1 on the cyclopentane nucleus, ready for chemical expansion to provide the α-chain of the selected target PG analog, and a hydroxyl group protected with p-methoxy benzyl at position 2.

Side chain expansion and derivatization can now take place using compound 18, advantageously expanding one side chain to that required in the target prostaglandin analog first, and subsequently expanding the second one to the target. Thus in the preferred embodiment where lubiprostone is the target compound, the α-chain is formed first. This is a linear heptanoic acid chain, which after formation merely needs simple protection of its terminal carboxylic acid group to confer stability and prevent its interference with other reactions. The ω-chain of lubiprostone is more chemically complex, involving a hemi-acetal and a di-fluorinated side chain. Introducing this chain second reduces the chances of fluorinated side chain losses in subsequent reactions, as the number of such reactions is reduced, the α-chain being already formed.

The first step in the α-chain expansion is reaction of compound 18 with (4-carboxybutyl)triphenylphosphonium bromide and sodium hexamethyl disilazane to cause opening of the lactone ring and condensation thereof to form a compound 20. This reaction suitably takes place in toluene solvent and at a temperature of −20 to −30° C., over a period of 2-3 hours. A double bond forms at position 5,6 of the side chain. Stereospecificity of the original Corey alcohol is retained.

This reaction is analogous to that conducted in known prostaglandin synthesis process, although according to the invention it is applied to novel reagents and produces novel intermediates. The next step is the protection of the terminal carboxylic acid group, and this is done in known manner, by reaction of compound 20 with benzyl bromide (BnBr) in the presence of potassium carbonate at room temperature in acetone solvent, in two steps, over 18 hours, producing protected acid compound 22. A 55-65% yield is typically obtained in this step.

Next, a double oxidation of hydroxyl groups to keto and aldehyde groups is conducted. Protected compound 22 is oxidized with pyridine-sulfur trioxide in the presence of diisopropylethylamine and DMSO and methylene chloride solvent. The result is oxidation of the primary alcohol side chain group to aldehyde, and oxidation of the secondary, nuclear alcohol group to a keto functionality, producing compound 24.

Now the fluorinated side chain required in lubiprostone can start to be introduced. Thus the next step in the process is the reaction of compound 24 with dimethyl-(2-oxo-3,3-difluoroheptyl)phosphonate (compound 26), in the presence of sodium hydride and dimethoxyethane (DME), for example at 50 to 70° over 18 hours. The result is compound 28, in 60-70% yield.

The final reactions in lubiprostone synthesis are the hydrogenation of the double bonds in compound 28, ((Z)-benzyl 7-((1R,2R,3R)-2-((E)-4,4-difluoro-3-oxooct-1-enyl)-3-(4-methoxybenzyloxy)-5-oxocyclopentyl)hept-5-enoate) which is itself a novel, inventive compound and a feature of the present invention, and the deprotection thereof to remove the carboxylic acid protectant from the α-chain terminus, and the removal of the p-methoxybenzyl (OPMB) protectant to form the desired hemi-acetal ring. This is done in a single step, by hydrogenation using hydrogen over palladium/carbon catalyst in isopropanol medium, at room temperature over, e.g., 2 hours. This process is another significant feature of the present invention. The product is lubiprostone, compound 30, in a 75-80% yield for this step.

The illustrated process is capable of producing lubiprostone from Corey alcohol in eight steps at an overall yield in excess of 15%, which is most acceptable in syntheses of this type and is significantly higher than that achieved with prior art processes. Most of the reagents used are relatively inexpensive, with the possible exception of dimethyl-(2-oxo-3,3-difluoroheptyl)phosphonate (compound 26). This is a known compound, preparable from ethyl 2-oxo-hexanoate by reaction with ethyl 2,2-difluorohexanoate he following reaction scheme:

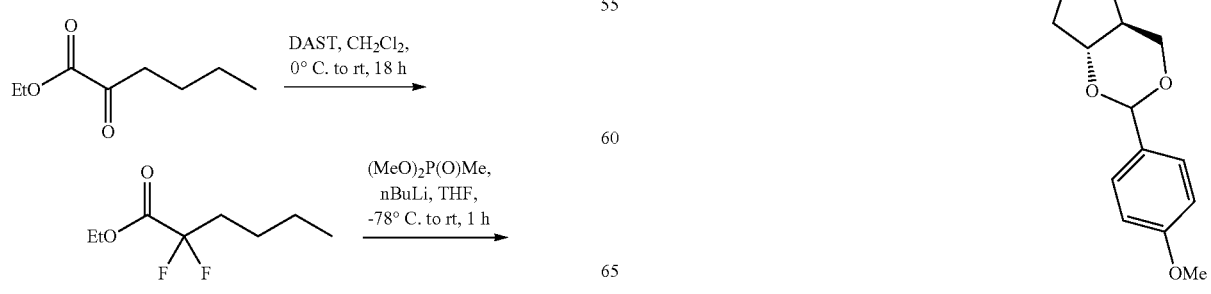

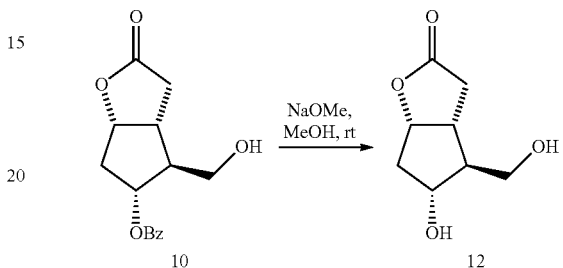

The specific preferred embodiment of the present invention is further described, for illustrative purposes, in the following specific experimental examples.

EXPERIMENTAL PROCEDURE

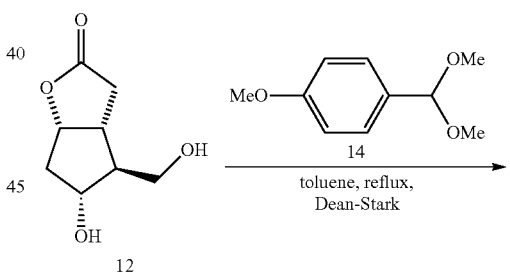

Corey Lactone Diol 12. To a suspension of 12 (15 g, 54 mmol, 1 equiv) in methanol (75 mL) was added sodium methoxide (25% wt in methanol, 1.2 mL, 5.4 mmol, 0.1 equiv). The mixture was stirred at room temperature for 1.5 h and then hydrochloric acid solution (4 M in dioxane, approximately 1 mL) was added until the pH was 3-4. The solution was stirred at room temperature for 10 min and then concentrated to dryness under vacuum on a rotary evaporator. The resulting white solid was suspended in methyl tert-butyl ether (150 mL) and stirred at room temperature for 1 h. The solid was filtered, washed with methyl tert-butyl ether, and dried under vacuum for 10 min to afford 9.1 g of 12 (97%) as a white solid.

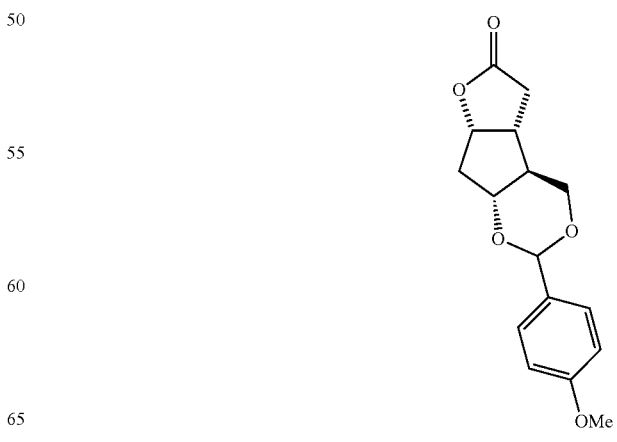

Protected Diol 16. To a suspension of 12 (5.0 g, 29 mmol, 1 equiv) in toluene (100 mL) was added anisaldehyde dimethyl acetal (14) (7.4 mL, 44 mmol, 1.5 equiv) and p-methoxy benzoic acid (44 mg, 0.29 mmol, 0.01 equiv). A condenser and a Dean-Stark apparatus were attached and the mixture was heated at 120° C. for 3 h while removing methanol by the Dean-Stark apparatus (approximately 2 mL). The reaction mixture was removed from the oil bath and stirred at room temperature for 15 min. Methyl tert-butyl ether (100 mL) was added and the mixture was cooled in an ice bath for 45 min. The resulting suspension was filtered, washed with methyl tert-butyl ether, and dried under vacuum for 10 min to afford 7.3 g of 16 (87%) as a white solid.

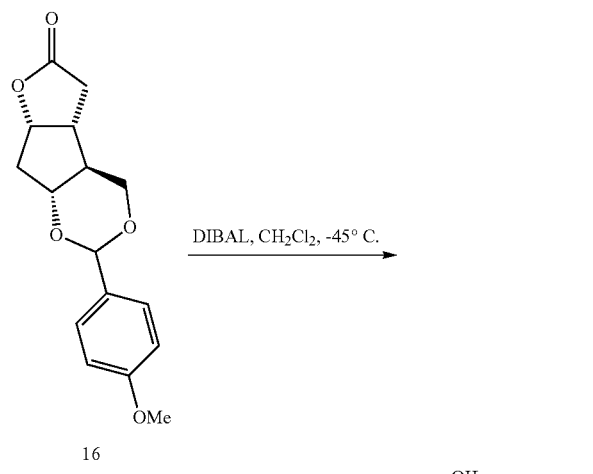

16

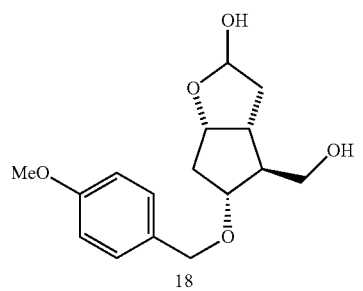

18

Lactol 18. A solution of 16 (14 g, 50 mmol, 1 equiv) in dichloromethane (500 mL) in a round-bottom flask containing a dropping funnel was flushed with $N_2$ for 5 min. The solution was cooled to −45° C. and diisobutylaluminum hydride (1 M in toluene, 150 mL, 150 mmol, 3 equiv) was added dropwise. The mixture was stirred for 1 hour and 20 min at −45° C. Buffer solution pH 7 (21 mL) was added dropwise and the solution was warmed to room temperature over 2 h. The suspension was filtered and washed with dichloromethane. The filtrate was concentrated to dryness under vacuum on a rotary evaporator to afford 13 g of 18 as a yellow oil (88% yield) which was used directly in the next step.

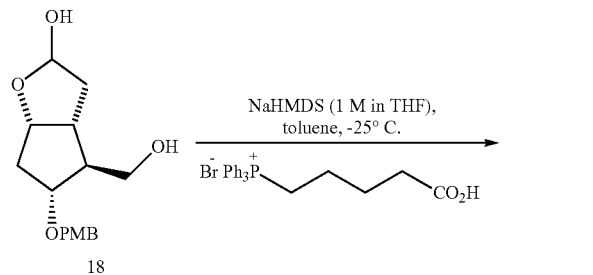

18

Diol 20. To a suspension of (4-carboxybutyl)triphenylphosphonium bromide (33 g, 75 mmol, 2 equiv) in toluene (220 mL) was added sodium hexamethyl disilazane (1 M in tetrahydrofuran, 262 mL, 262 mmol, 7 equiv). The mixture was stirred at room temperature for 1 h and then cooled to −25° C. Compound 18 in tetrahydrofuran (60 mL) was added dropwise and then warmed to room temperature over 4 h. Water (200 mL) was added and the organic layer was separated and extracted with water (2×50 mL). The aqueous washings were combined and 20% aqueous citric acid solution (125 mL) was added. The suspension was extracted with dichloromethane (4×100 mL). The organics were combined, dried over sodium sulfate, filtered, and concentrated to dryness under vacuum on a rotary evaporator to afford a yellow oil containing 20. The oil was dissolved in acetone (433 mL) and potassium carbonate (11 g, 77 mmol, 2 equiv) and benzyl bromide (9.1 mL, 77 mmol, 2 equiv) were added. The mixture was stirred at room temperature for 18 h, filtered, and concentrated to dryness under vacuum on a rotary evaporator. The crude oil was purified by column chromatography using 50% ethyl acetate/hexanes as eluant to afford 11 g of 22 as a yellow oil (64%).

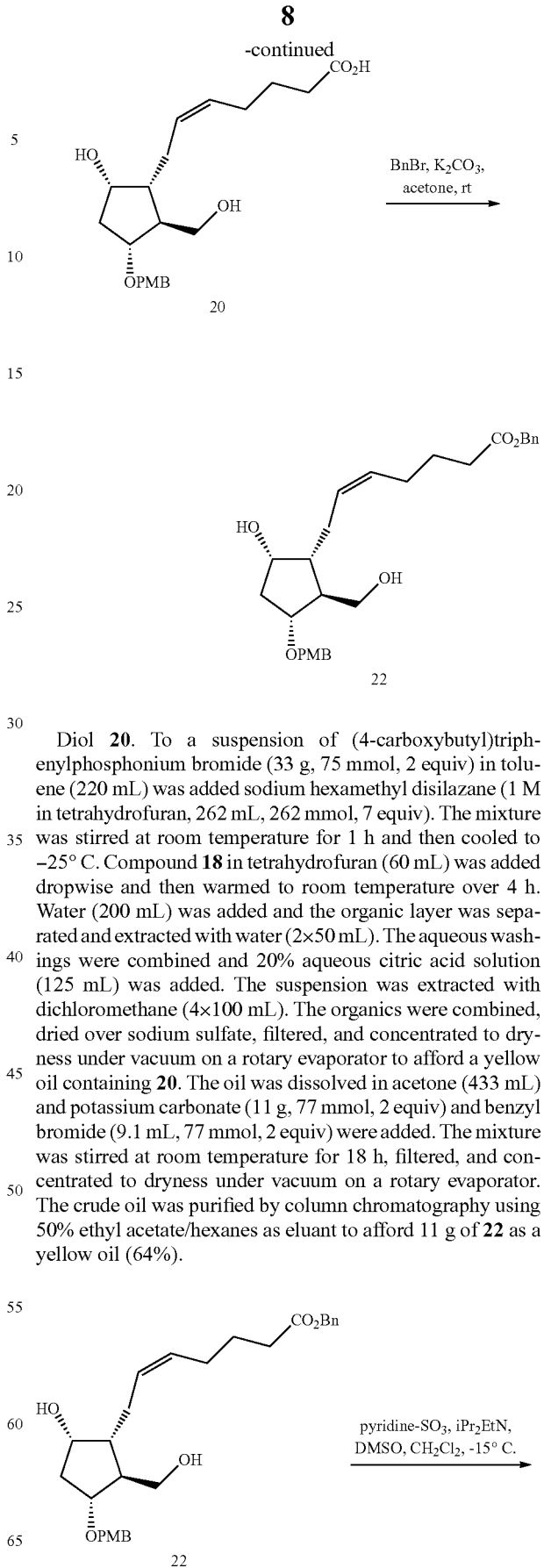

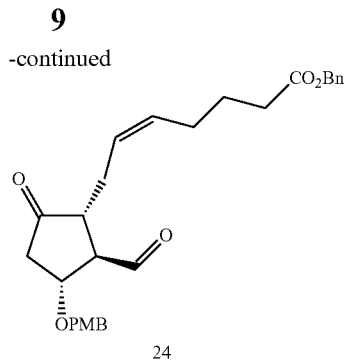

24

Aldehyde 24. A solution of 22 (3.5 g, 7.4 mmol, 1 equiv) and dimethyl sulfoxide (10.5 mL) in dichloromethane (70 mL) was cooled to −15° C. Diisopropyl ethylamine (4.3 mL, 45 mmol, 6 equiv) was added followed by the addition of a solution of sulfur trioxide pyridine complex (7.1 g, 45 mmol, 6 equiv) in dimethyl sulfoxide (21 mL). The mixture was stirred at −15° C. for 1 h and was then diluted with 20% aqueous citric acid solution (20 mL). The aqueous layer was extracted with dichloromethane (3×20 mL) and the organics were combined, dried over sodium sulfate, filtered, and concentrated to dryness under vacuum on a rotary evaporator. The crude oil was purified by column chromatography using 20-40% ethyl acetate/hexanes as a gradient eluant to afford 3.1 g of 24 as a yellow oil (90%).

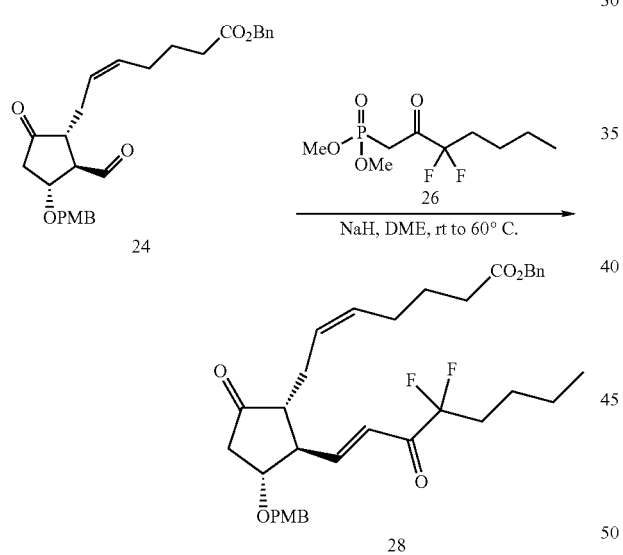

Protected Unsaturated Lubiprostone 28. A suspension of sodium hydride (60% dispersion in oil, 2.1 g, 53 mmol, 2.5 equiv) in tetrahydrofuran (500 mL) was added dropwise a solution of 26 (14 g, 53 mmol, 2.5 equiv) in tetrahydrofuran (165 mL). The mixture was stirred for 1 h at room temperature. A solution of 24 (9.9 g, 21 mmol, 1 equiv) in tetrahydrofuran (165 mL) was added dropwise. The mixture was then heated with stirring at 58° C. for 2 days. The mixture was cooled to room temperature and saturated aqueous ammonium chloride (200 mL) was added followed by water (200 mL). The aqueous layer was separated and extracted with ethyl acetate (3×150 mL). The organics were combined, dried over sodium sulfate, filtered, and concentrated to dryness under vacuum on a rotary evaporator. The crude oil was purified by column chromatography using 10-25% ethyl acetate/hexanes as a gradient eluant followed by a second column chromatography using 20% ethyl acetate/hexanes as to afford 7.8 g of 28 as a yellow oil (61%).

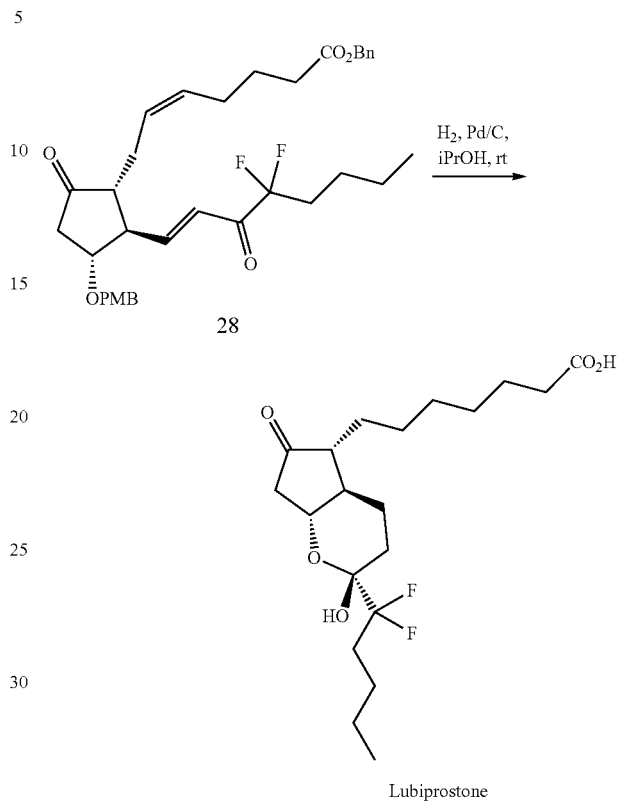

Lubiprostone

Lubiprostone. A mixture of 28 (8.0 g, 13 mmol, 1 equiv) and 5% palladium on carbon (containing 54.02% water, 5.1 g, 1.3 mmol, 0.1 equiv) in isopropanol (300 mL) was stirred under an atmosphere of $H_2$ (g) in a Parr hydrogenator at 40 psi for 2 h. The solution was then filtered through Celite™ and washed with methyl tert-butyl ether. The filtrate was concentrated to dryness under vacuum on a rotary evaporator and the resulting yellow oil was purified by a silica plug by first eluting with dichloromethane to remove impurities and then with methyl tert-butyl ether to remove the product. The methyl tert-butyl ether filtrate was concentrated to dryness under vacuum on a rotary evaporator to afford a yellow oil that was dried under vacuum for 3 h. The resulting oil was dissolved in dichloromethane (5 mL) with heating and a 1:1 solution of hexanes:petroleum ether (50 mL) was added. The solution was placed in an ice bath and stirred vigorously. Methyl tert-butyl ether (1 mL) was added and the product began precipitating out of solution. The mixture was stirred for 2 h, filtered, and washed with a solution of 2% dichloromethane in 1:1 mixture hexanes:petroleum ether to afford 4.1 g of Lubiprostone (78%) as a white solid.

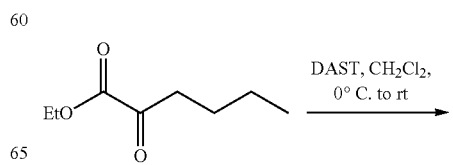

-continued

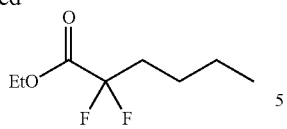

Ethyl 2,2-Difluorohexanoate. To a 0° C. solution of ethyl 2-oxohexanoate (6.3 g, 40 mmol, 1 equiv) in dichloromethane (125 mL) was added dropwise (diethylamino)sulfur trifluoride (6.3 mL, 48 mmol, 1.2 equiv). The solution was warmed to room temperature over 4 h. Saturated aqueous sodium bicarbonate (100 mL) was slowly added. The aqueous layer was separated and extracted with dichloromethane (3×50 mL). The organics were combined, dried over sodium sulfate, filtered, and concentrated to dryness under vacuum on a rotary evaporator to afford 6.5 g of ethyl 2,2-difluorohexanoate (91%) as a yellow oil.

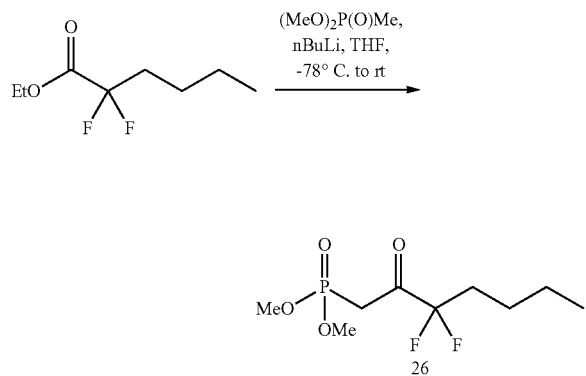

Dimethyl-(2-oxo-3,3-difluoroheptyl)phosphonate 26. A solution of dimethyl methylphosphonate (6.5 g, 80 mmol, 2.2 equiv) in tetrahydrofuran (100 mL) was cooled to −78° C. and n-butyllithium (2.5 M in hexanes, 14 mL, 36 mmol, 1 equiv) was added dropwise. The solution was stirred at −78° C. for 30 min and ethyl 2,2-difluorohexanoate (6.5 g, 36 mmol, 1 equiv) was added dropwise. The solution was stirred at −78° C. for 1 h and warmed to 0° C. over 1 h. Pentane (100 mL) was added followed by the dropwise addition of 2M $H_2SO_4$ to pH=6. The aqueous layer was separated and extracted with pentane (3×15 mL). The organics were combined, dried over sodium sulfate, filtered, and concentrated to dryness under vacuum on a rotary evaporator. The crude oil was purified by column chromatography using methyl tert-butyl ether as eluant to afford 4.1 g of 26 as a yellow oil (44%).

What is claimed is:

1. A fused cyclopentane—4-substituted 3,5-dioxalane lactone compound useful as an intermediate in the synthesis of prostaglandin analogs, the compound having the formula A:

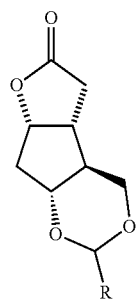

(A)

wherein R represents an aryl group.

2. Compound A according to claim 1 wherein R represents a substituted phenyl group.

3. Compound A according to claim 1 wherein R represents p-methoxyphenyl.

4. A substituted cyclopentane lactone compound useful as an intermediate in the synthesis of prostaglandin analogs, the compound having the formula B:

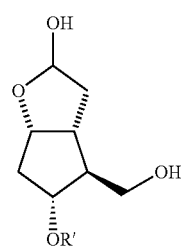

(B)

wherein R' represents a lower alkoxy substituted benzyl group.

5. Compound B according to claim 4 wherein R' represents p-methoxybenzyl.

6. Compound C, ((Z)-benzyl 7-((1R,2R,3R)-2-((E)-4,4-difluoro-3-oxooct-1-enyl)-3-(4-methoxybenzyloxy)-5-oxocyclopentyl)hept-5-enoate), of formula:

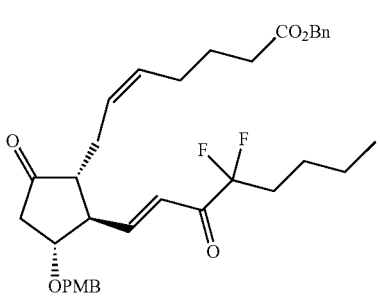

(C)

\* \* \* \* \*